Figure 1:
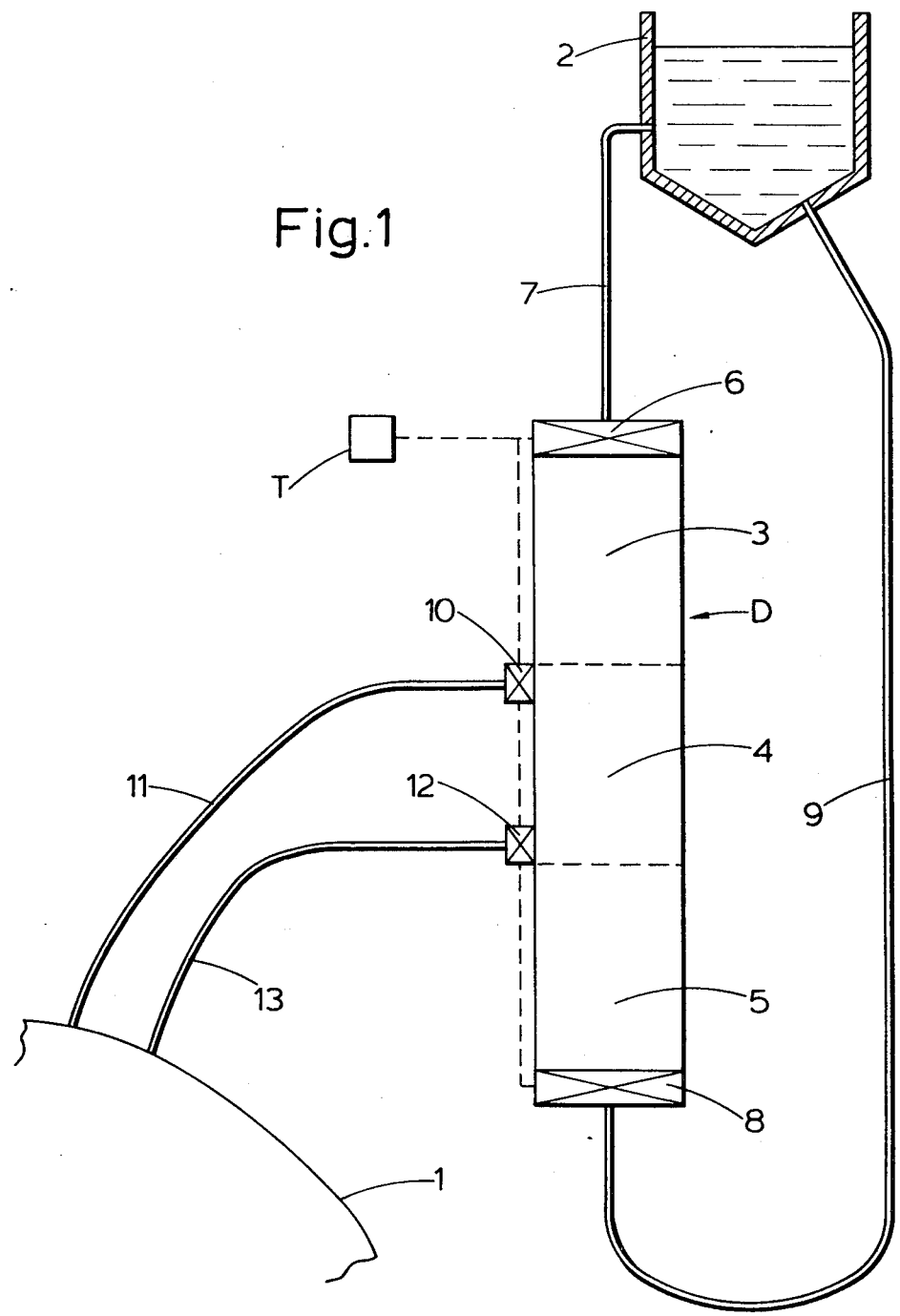

United States Patent [19]

Elliott

[11] 4,453,574

[45] Jun. 12, 1984

[54] DISPENSING OF LIQUIDS

[75] Inventor: Leonard G. Elliott, Ulverston, England

[73] Assignee: Glaxo Group Limited, London, England

[21] Appl. No.: 256,402

[22] Filed: Apr. 22, 1981

[30] Foreign Application Priority Data

Apr. 22, 1980 [GB] United Kingdom ............. 8013254

[51] Int. Cl.³ .............................................. B65B 3/04
[52] U.S. Cl. ......................................... 141/5; 141/37;
222/433; 435/287
[58] Field of Search ....................... 222/432, 433;
141/1–12, 37–82; 435/287

[56] References Cited

U.S. PATENT DOCUMENTS

| 7999 | 3/1851 | Stevens | 222/433 |
| 1,673,305 | 6/1928 | Yont et al. | 222/433 |
| 2,877,929 | 3/1959 | Ireland | 222/1 |

FOREIGN PATENT DOCUMENTS 1079850 3/1955 Fed. Rep. of Germany .

*Primary Examiner*—Houston S. Bell, Jr.

*Attorney, Agent, or Firm*—McAulay, Fields, Fisher, Goldstein & Nissen

[57] ABSTRACT

Liquid additives can be supplied to a fermenter vessel from a reservoir by a dispensing device which comprises a central discharge chamber connected in series between an upper escape chamber and a lower inlet chamber. These chambers are arranged to provide a smooth passage for liquid and do not have any steps or recesses therein. An escape port leading from the upper end of the escape chamber to the reservoir is controlled by a valve member. An inlet port leads into the lower end of the inlet chamber from the reservoir and is controlled by a valve member. A discharge port leads from the bottom end of the discharge chamber and is controlled by a valve member. A pressure equalizing port leads to the top end of the discharge chamber and is controlled by a valve member. The discharge and pressure equalizing ports are connected to the upper portion of the fermenter vessel. The escape chamber is capable of retaining liquid therein by interfacial tension while liquid is discharged from the discharge chamber. If desired, the discharge chamber may be divided into a plurality of sub-chambers.

7 Claims, 4 Drawing Figures

DISPENSING OF LIQUIDS

BACKGROUND OF THE INVENTION

An object of the invention is to provide a way of dispensing small measured volumes of a liquid additive from a reservoir at atmospheric pressure to a fermenter vessel under pressure with great accuracy. By "small" is meant quantities in the range 0.4 to 10 ml. and the pressure of the vessel may be of the order of 3 bar. The invention is particularly, but not exclusively, applicable to the dispensing of measured quantities of an additive, for example, a nutrient, to a fermenter vessel.

BRIEF SUMMARY OF THE INVENTION

A device for dispensing measured volumes of liquid to a vessel under higher pressure, comprises a central metering and discharge chamber (hereinafter called the discharge chamber) arranged between, and connected in series with, an inlet chamber and an escape chamber, a discharge port at the inlet chamber end of the discharge chamber and a pressure equalising port at the other end of the discharge chamber, the said chambers being arranged to provide a smooth passage for liquid without steps therein and the inlet and escape chambers respectively having inlet and escape ports each controlled by valve members, a valve member controlling the discharge port, and a valve member controlling the pressure equalising port, the said escape chamber being capable of retaining liquid therein by interfacial tension when liquid is being discharged from the discharge chamber. In one preferred embodiment, the escape chamber is of circular cross-section and has a diameter not greater than five millimeters, preferably three millimeters.

Flexibility in the choice of the size of the measured quantity dispensed may be obtained by constructing the central discharge chamber as a plurality of sub-chambers (which may be of different cross-sectional areas and/or lengths) inter-connected in series each sub-chamber having its own valve member and discharge port.

The valve members are preferably operable by electric solenoids under the control of a timing device.

If desired, the device may be provided by a series of valve chambers each of which has two main ports leading out of the valve chamber in opposite directions and an additional port controlled by a valve member, an inlet valve chamber having a main port connected with the main port at one end of the series of chambers and an inlet port controlled by a valve member, and an escape valve chamber having a main port connected with the main port at the other end of the series of chambers and having an escape port controlled by a valve member, the said main ports of the various valve chambers being connected together so that with the valve chambers and valve members they provide a smooth passage for liquid without any steps or recesses therein, the said escape chamber being capable of retaining liquid therein by interfacial tension when liquid is being discharged from the discharge chamber and each of the valve members being operable by an electric solenoid under the control of an electric timing device.

Alternatively, the various chambers and ports may be located in a single block.

The invention also provides a fermenter apparatus which includes a fermenter vessel, a reservoir for a liquid additive to be supplied to the fermenter vessel and a dispensing device according to the invention, the dispensing device being so arranged that the escape chamber is above, and the inlet chamber is below, the discharge chamber, the escape port leads from the upper end of the escape chamber to the reservoir, the inlet port leads into the lower end of the inlet chamber from the reservoir, the discharge port leads from the bottom end of the discharge chamber to the upper portion of the fermenter vessel, the pressure equalising port leads to the top end of the discharge chamber and is connected to the upper portion of the fermenter vessel.

The central discharge chamber may be composed of a plurality of sub-chambers each with its own discharge port controlled by a valve member. The discharge ports of these sub-chambers may be connected to a common manifold leading to the fermenter vessel. The various valve members may be operable by electric solenoids, if desired, controlled by a timing device.

The invention also provides a method in which the dispensing device is used to feed a measured volume of a liquid from a reservoir to a vessel at higher pressure, the said method comprising the steps of opening the escape port while all other parts are closed thereby to allow gas to escape so as to equalise the pressure in the chamber to that of the reservoir, opening the inlet port to the inlet chamber to permit the passage of liquid additive from the reservoir to the bottom of the system while gas can continue to escape from the escape port of the escape chamber so that liquid rises through the chambers until they are completely filled with liquid, then closing the escape port and the inlet port, opening the pressure equalising port and the discharge port thereby to allow liquid to flow from the discharge chamber into the vessel, while retaining liquid in the escape chamber by interfacial tension and retaining liquid in the lower chamber and then, when the discharge chamber is completely emptied, closing the pressure equalising port and the discharge port. If desired, the method may be carried out with a dispensing device in which the discharge chamber is composed of a plurality of sub-chambers each of which has its own discharge port. Liquid may be discharged from a selected one, or ones, of these sub-chambers as desired so that the measured volume dispensed may be varied.

BRIEF DESCRIPTION OF THE ACCOMPANYING SCHEMATIC DRAWINGS

Figure 2:
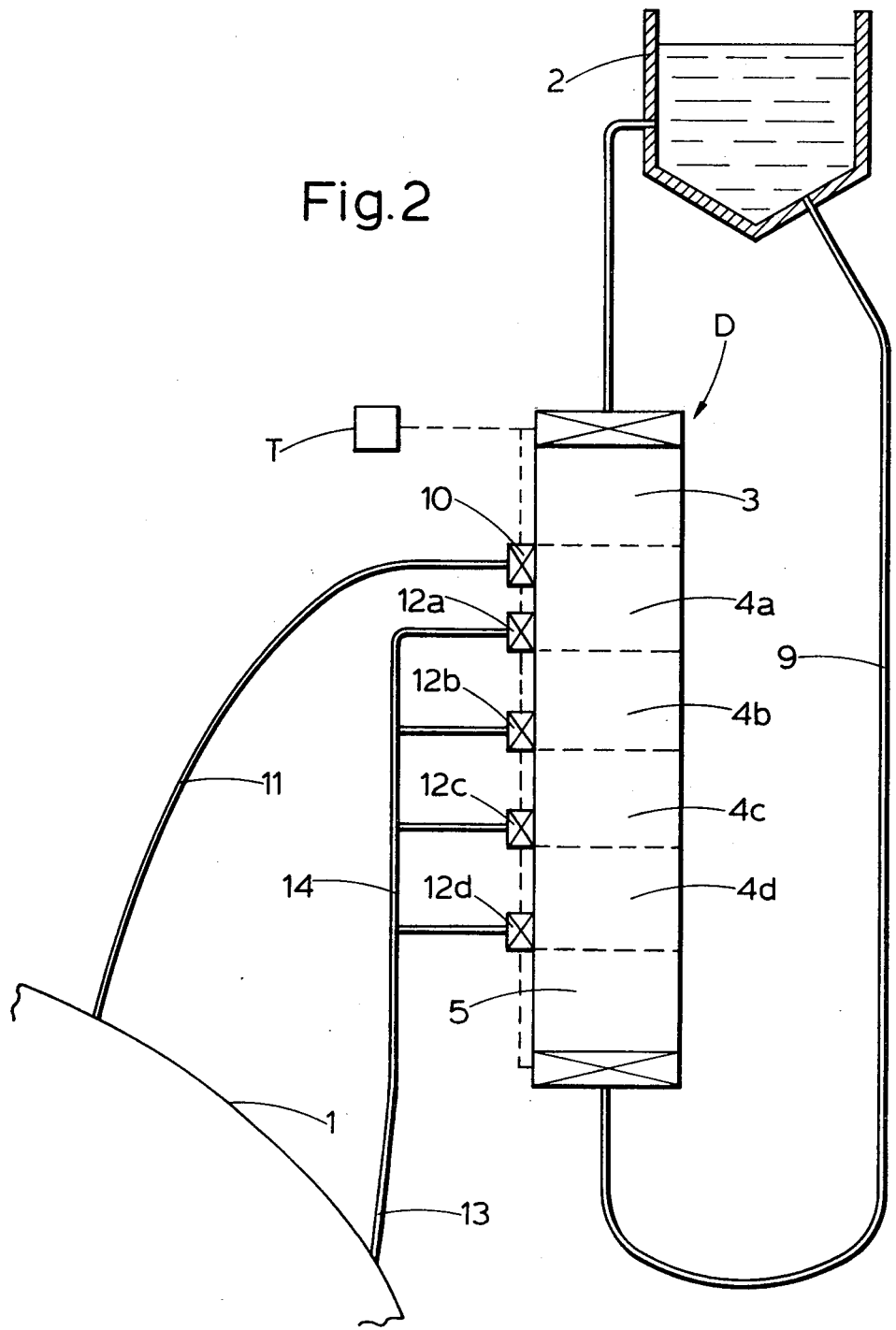
Figure 3:
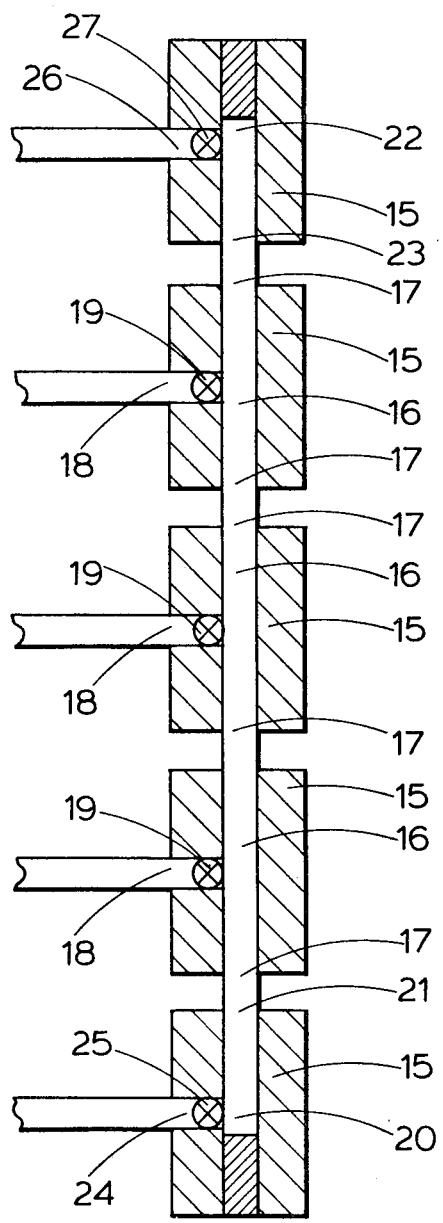
Figure 4:
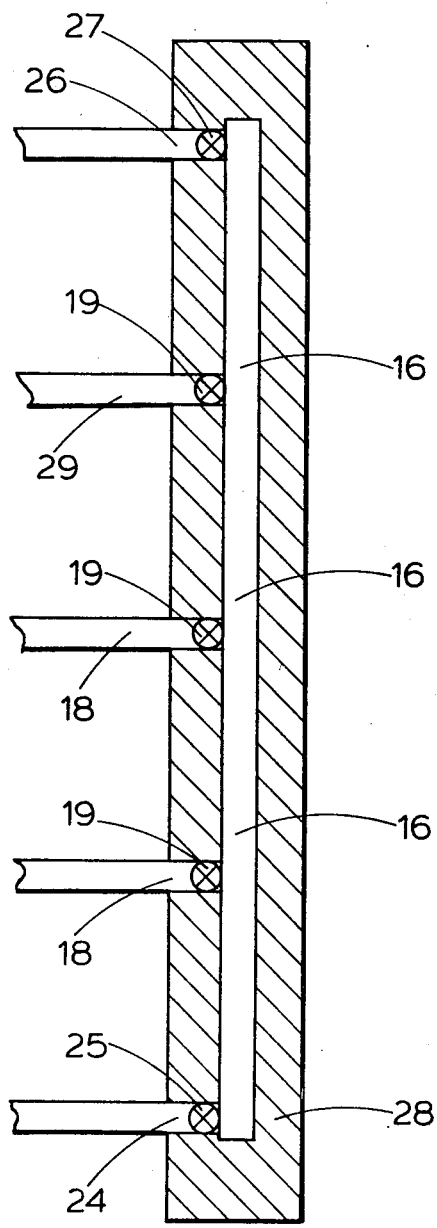

FIGS. 1 and 2 each illustrate a fermenter apparatus and,

FIGS. 3 and 4 are sectional views of alternative dispensing devices.

DESCRIPTION OF SOME PREFERRED EMBODIMENTS

The apparatus illustrated in FIG. 1 comprises a fermenter vessel 1 and a reservoir 2, with sterile venting means (not illustrated), for liquid and a dispensing device generally designated D. The fermenter vessel may contain a fermentation broth and the reservoir may contain a liquid such as water or a nutrient which may be a solution of salts or sugar, or a suitable oil, or a fine suspension. The vessel 1 may be at pressure of about 3 bar while the reservoir 2 will be at atmospheric pressure. The present invention is concerned with the means for dispensing the liquid to the vessel 1. The dispensing device D illustrated in FIG. 1 comprises three chambers 3, 4 and 5. These three chambers are arranged in series one above the other. The lower chamber 5 is an inlet chamber, the central chamber 4 is a metering and discharge chamber and the upper chamber 3 is an escape chamber. A valve member 6 controls an escape port at the top of the escape chamber 3 which is connected by a line 7 to the reservoir 2. A valve member 8 controls a port at the lower end of the inlet chamber 5 which is connected by a feedline 9 to the reservoir 2. The entry from the reservoir to the feedline 9 is at a lower level than the entry to the line 7. Thus, liquid enters the dispensing device through the inlet port at the bottom of the device. The discharge chamber 4 has an upper pressure equalising port controlled by a valve member 10 and connected by a line 11 with the vessel 1 and also has a discharge port controlled by a valve member 12 which is connected by a line 13 with the vessel 1. The chamber 4 has a volume equal to the measured quantity of liquid (hereinafter called the "shot") intended to be discharged into the vessel 1. The chambers 3, 4 and 5 are so arranged that together they provide a smooth passage for liquid which is free of any steps or recesses. The cross-section of the passage in the chamber 3 is such that liquid will be retained in the chamber by interfacial tension while liquid is discharged from the chamber 4.

The various valve members are arranged to close bubble-tight at working pressure, e.g. a pressure of 3 bar. The valve members are controlled by electric solenoids connected to a suitable timer device T so as to operate in a desired sequence. The various valve members are capable of operating under conditions of sterilisation and the system can be sterilised in situ by steam at a pressure in slightly excess of 1 bar e.g. 121° C. at 1.034 bar.

A shot of liquid is dispensed to the vessel 1 by operation of the system in the following sequence.

At the commencement of the sequence all the valve members of the system are in a position to close the respective ports. At the commencement of a cycle, the uppermost valve member 6 opens (all the other valve members being closed) so that expanding gas can escape from the system to the reservoir. This reduces the pressure in the system to that of the liquid head in the reservoir. The valve member 8 controlling the inlet port then opens so that liquid runs from the reservoir through the line 9 and into the inlet chamber 5. During this time, gas continues to escape to the reservoir through the escape port controlled by the valve member 6 and liquid rises through the system. When the system is full of liquid, the valve members 6 and 8 close in a bubble-tight manner. The valve members 10 and 12 are then operated to open their respective ports so that liquid can be discharged from the chamber 4 through the line 13 into the vessel 1. During the period of such discharge, liquid in the escape chamber 3 is held therein by interfacial tension. When the discharge has been completed the valve members 10 and 12 close, leaving the system at the pressure of the fermenter vessel. This sequence may then be repeated. The various valve members ar controlled by electric solenoids connected to the timer T.

FIG. 2 illustrates a modified device in which the discharge chamber is composed of sub-chambers 4a to 4d inclusive. A pressure equalising port controlled by valve member 10 leads into the top of the upper sub-chamber 4a. Each sub-chamber has a discharge port controlled by valve members 12a to 12d inclusive leading to a common manifold 14 connected by line 13 to the vessel 1.

The various sub-chambers 4a to 4d may be of different volumes. This system enables shots of different volume to be discharged as desired. For example, to obtain the largest possible shot, the bottom valve member 12d is moved to the open position and all the other valve members 12a to 12c are closed when a charge is desired. For the smallest possible shot, the upper valve member 12a is opened and all the other valve members 12b to 12d are closed.

As shown in FIG. 3, the device may be built up from a series of valve bodies 15. Each of the central valve bodies 15 has a chamber 16 with two opposed main ports 17 which lead into the chamber, these main ports being connected with the main ports of the neighbouring valve bodies. An addition port 18 communicates with each valve chamber 16 and is associated with valve member 19. An inlet chamber 20 has a main port 21 connected with the main port 17 at one end of the series of chambers. An escape member 22 has a main port 23 connected with the main port 17 at the other end of the series of chambers. An inlet port 24 leads into the inlet chamber 20 and has a valve member 25. An escape port 26 having a valve member 27 leads out of the escape chamber 22. All the valve members are displaceable by electric solenoids. All the valve chambers and valve members are arranged so as to provide a common smooth flow passage for liquid without any steps or recesses therein. The cross-sectional area of the escape chamber is such that liquid is retained in the chamber by interfacial tension when liquid is being discharged from the discharge chamber.

FIG. 4 illustrates a modification of the device illustrated in FIG. 3 in which the device, instead of being built up from a series of separate valve bodies, is constructed from a single block. In this Figure, ports similar to those illustrated in FIG. 3 have the same reference numerals. In the construction illustrated in FIG. 4, a single central chamber 16 extends through a block 28. The inlet port 24 leads into the lower end of the chamber 16 and the escape port 26 leads out of the upper end of the chamber 16. A plurality of ports 18 extend from the chamber 16 and serve as discharge ports. A further similar port 29 is a pressure equalising port. All of the ports 18 or 29 are associated with valve members 19 displaceable by electric solenoids. The central chamber 16 and the valve members 19, 25 and 27 are arranged to provide a smooth flow passage for liquid and has no steps or recesses therein.

The portion of the central chamber 16 between the escape port 26 and the pressure equalising port 29 constitutes an escape chamber having a cross-sectional area such that liquid is retained in that portion of the chamber by interfacial tension when liquid is discharged through the ports 18.

I claim:

1. A device for dispensing measured volumes of liquid to a vessel under higher pressure, the said device comprising a central discharge chamber arranged between, and connected in series with, an inlet chamber at one end, and an escape chamber at the other end, a discharge port at the inlet chamber end of the discharge chamber and a pressure equalising port at the other end of the discharge chamber, the said chambers having walls arranged to provide a smooth passage for liquid without steps therein, and the inlet and escape chambers respectively having inlet and escape ports each controlled by valve members, a valve member controlling the discharge port, and a valve member controlling the pressure equalising port, the said escape chamber being sized to retain liquid therein by interfacial tension when liquid is being discharged from the discharge chamber.

2. A device as claimed in claim 1, wherein the discharge chamber is composed of a plurality of sub-chambers interconnected in series, each sub-chamber having its own valve member and discharge port.

3. A device as claimed in claim 1, wherein the escape chamber has a circular cross-section of not more than five millimeters diameter.

4. A device as claimed in claim 1, wherein the escape chamber has a circular cross-section of three millimeters diameter.

5. A device as claimed in claim 1, wherein the discharge chamber comprises a plurality of valve chambers each of which has two main ports which lead out of the valve chamber in opposite directions and which has an additional port controlled by a valve member, all of the valve chambers being connected together in series, wherein the inlet chamber is a valve chamber arranged with a main port connected with the main port at one end of the discharge chamber and having an additional port serving as the inlet port and wherein the escape chamber is a similar valve chamber having a main port connected with the main port at the other end of the discharge chamber and having an additional port serving as an escape port.

6. A device as claimed in claim 1, comprising a single body with a central chamber therein, an inlet port leading into an end of the central chamber, an escape port leading from the other end of the central chamber, a plurality of discharge ports leading from the central chamber at positions between the inlet and escape ports, a pressure equalising port leading from the central chamber at a position between the escape port and the plurality of discharge ports, and a plurality of valve members one of which is associated with each of the said ports.

7. A method of feeding a measured volume of a liquid from a reservoir to a vessel at higher pressure in which said liquid is dispensed from a dispensing device as claimed in claim 1, said method comprising the steps of opening the escape port while all the other ports are closed thereby to allow gas to escape so as to equalise the pressure in the chamber to that of the reservoir, opening the inlet port to the inlet chamber to permit the passage of liquid additive from the reservoir to the bottom of the system while the gas can continue to escape from the escape port of the escape chamber so that liquid rises through the chambers until they are completely filled with liquid, then closing the escape port and the inlet ports, opening the pressure equalising port and the discharge port thereby to allow liquid to flow from the discharge chamber into the vessel while retaining liquid in the escape chamber by interfacial tension and retaining liquid in the lower chamber and then, when the discharge chamber is completely emptied, closing the pressure equalising port and the discharge port.

* * * * *